United States Patent [19]

Ueda et al.

[11] Patent Number: 4,579,859
[45] Date of Patent: Apr. 1, 1986

[54] VASODILATING TRINITRATOALKYL ESTERS OF 2-CYANO-1,4-DIHYDROPYRIDINES

[75] Inventors: Ikuo Ueda, Toyonaka; Daizo Morino, Matsubara; Koichi Takimoto, Takarazuka, all of Japan

[73] Assignee: Fujisawa Pharmaceutical Co., Ltd., Osaka, Japan

[21] Appl. No.: 611,529

[22] Filed: May 17, 1984

[30] Foreign Application Priority Data

May 27, 1983 [GB] United Kingdom ............... 8314744

[51] Int. Cl.$^4$ ................. A61K 31/455; C07D 211/90; C07D 401/04
[52] U.S. Cl. .................................. 514/344; 546/286; 546/321; 546/257; 546/258
[58] Field of Search ............... 424/266; 546/286, 257, 546/258, 321; 514/344

[56] References Cited

U.S. PATENT DOCUMENTS

| | | | |
|---|---|---|---|
| 3,427,295 | 2/1969 | Reed | 260/467 |
| 4,370,334 | 1/1983 | Sato | 546/321 |
| 4,423,052 | 12/1983 | Araki et al. | 546/321 |
| 4,472,411 | 9/1984 | Hatayama et al. | 546/321 |

FOREIGN PATENT DOCUMENTS 2117571 10/1972 Fed. Rep. of Germany .

OTHER PUBLICATIONS

Bossert, et al., "4 Aryldihydropyridines", Angew. Chem. Int. Ed. Engl. 20, 762–769 (1981).
Schramm, et al., "Novel Dihydropyridines with Positive Inotropic Action", Nature vol. 303 (9 Jun. 1983) pp. 535–537.

*Primary Examiner*—Henry R. Jiles
*Assistant Examiner*—Dale A. Bjorkman
*Attorney, Agent, or Firm*—Oblon, Fisher, Spivak, McClelland & Maier

[57] ABSTRACT

The invention relates to novel dihydropyridine derivatives of vasodilating activity of the formula:

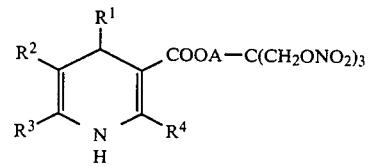

in which $R^1$ is aryl selected from the group consisting of phenyl, tolyl, xylyl, cumenyl and mesityl which may have one or more substituents selected from the group consisting of halogen, nitro, hydroxy, carboxy and lower alkoxy, or a heterocyclic group containing at least one hetero atom selected from the group consisting of oxygen, nitrogen and sulfur, $R^2$ is lower alkoxy-carbonyl or N,N-disubstituted amino(lower)alkoxycarbonyl, $R^3$ is lower alkyl, alkanoyl, protected alkanoyl or cyano, $R^4$ is lower alkyl and A is lower alkylene, and pharmaceutically acceptable salt thereof.

6 Claims, No Drawings

VASODILATING TRINITRATOALKYL ESTERS OF 2-CYANO-1,4-DIHYDROPYRIDINES

This invention relates to 2,6-disubstituted-1,4-dihydropyridine derivative and a pharmaceutically acceptable salt thereof. More particularly, it relates to novel 2,6-disubstituted-1,4-dihydropyridine derivative and a pharmaceutically acceptable salt thereof which have vasodilating activities, to a process for the preparation of the same, to a pharmaceutical composition comprising the same and to a method for the treatment of cardiovascular disorder and hypertension in human being.

One object of this invention is to provide the novel and useful 2,6-disubstituted-1,4-dihydropyridine derivative and a pharmaceutically acceptable salt thereof, which are structurally characterized in the substituent at the third position of the dihydropyridine nucleus and have stronger activity as compared with the known compounds, for example, Nifedipine worldwidely put on the market.

Another object of this invention is to provide a process for the preparation of said 2,6-disubstituted-1,4-dihydropyridine derivative and a pharmaceutically acceptable salt thereof.

A further object of this invention is to provide a pharmaceutical composition comprising, as an active ingredient, said 2,6-disubstituted-1,4-dihydropyridine derivative and a pharmaceutically acceptable salt thereof, which are useful as a vasodilator.

Still further object of this invention is to provide a therapeutical method for treatment of cardiovascular disorder such as coronary insufficiency, angina pectoris or myocardial infarction and hypertension.

The 2,6-disubstituted-1,4-dihydropyridine derivative of this invention can be represented by the following formula:

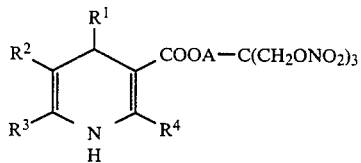

in which
R¹ is aryl which may have one or more suitable substituent(s) or a heterocyclic group,
R² is an esterified carboxy group,
R³ is lower alkyl, acyl, protected acyl or cyano,
R⁴ is lower alkyl and
A is lower alkylene.

With regard to the object compound illustrated by the above formula (I), it is to be understood that there can be a pair of two optical isomers due to the asymmetric carbon atom at the fourth position of the dihydropyridine nucleus, and accordingly these types of isomers are to be included within the scope of this invention and represented by the same single formula (I), inclusively.

Suitable pharmaceutically acceptable salt of the object compound (I) is conventional non-toxic salt and include an acid addition salt such as an organic acid addition salt (e.g. acetate, trifluoroacetate, maleate, tartarate, methanesulfonate, benzenesulfonate, formate, toluenesulfonate, etc.), an inorganic acid addition salt (e.g. hydrochloride, hydrobromide, hydroiodide, sulfate, nitrate, phosphate, etc.), or a salt with an acidic amino acid (e.g. aspartic acid, glutamic acid, etc.), and the like.

According to this invention, the object compound (I) can be prepared by the processes as illustrated by the following schemes.

Process 1: (1)

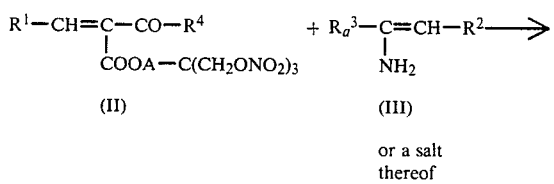

or a salt thereof

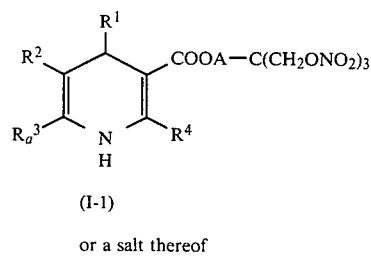

or a salt thereof

Process 2: (2)

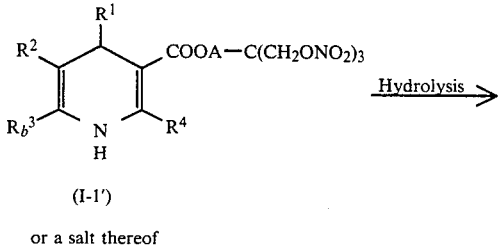

or a salt thereof

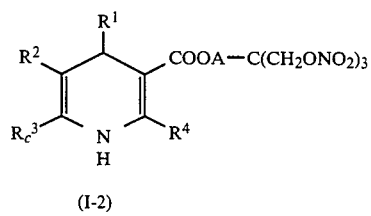

or a salt thereof

Process 3: (3)

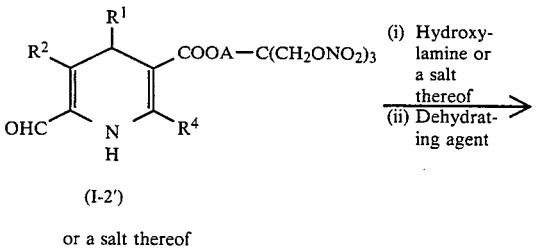

or a salt thereof

-continued

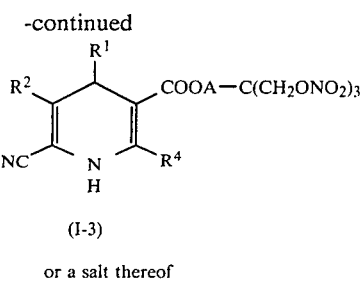

(I-3)

or a salt thereof in which
R¹, R², R⁴ and A are each as defined above,
$R_a^3$ is lower alkyl or protected acyl,
$R_b^3$ is protected acyl, and
$R_c^3$ is acyl.

With regard to the starting compounds (II) and (III), some of said compounds are novel and can be prepared by the following processes A and B or a conventional manner.

Process A: (A)

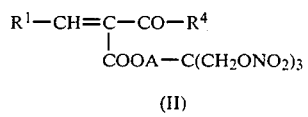

(II)

Process B: (B)

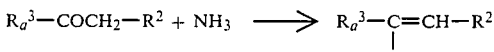

or a salt thereof
or a salt thereof in which R¹, R², $R_a^3$, R⁴ and A are each as defined above.

In the above and subsequent descriptions of the present specification, suitable examples and illustrations of the various definitions which the present invention include within the scope thereof are explained in details as follows.

The term "lower" is intended to mean 1 to 6 carbon atoms, unless otherwise indicated.

Suitable "aryl which may have one or more suitable substituent(s)" for R¹ may include phenyl, tolyl, xylyl, cumenyl, mesityl, and the like, which may have one to five, preferably one to two suitable substituent(s) such as halogen (e.g. chlorine, bromine, fluorine, iodine, etc.), nitro, hydroxy, carboxy, lower alkoxy (e.g. methoxy, ethoxy, propoxy, isopropoxy, butoxy, pentyloxy, hexyloxy, etc.) and the like. The preferred examples of said definition may be dihalophenyl (e.g. 2,3-dichlorophenyl, etc.), nitrophenyl (e.g. 3-nitrophenyl, etc.).

Suitable "heterocyclic group" for R¹ may include aromatic heterocyclic group containing at least one hetero atom such as oxygen atom, nitrogen atom and sulfur atom, and the preferred examples thereof may be 6-membered aromatic heterocyclic group containing a nitrogen atom such as pyridyl (e.g. 4-pyridyl, etc.).

Suitable "esterified carboxy group" for R² may include lower alkoxycarbonyl (e.g. methoxycarbonyl, ethoxycarbonyl, propoxycarbonyl, isopropoxycarbonyl, butoxycarbonyl, tert-butoxycarbonyl, pentyloxycarbonyl, neopentyloxycarbonyl, hexyloxycarbonyl, etc.), N,N-disubstituted amino(lower)alkoxycarbonyl, for example, N-lower alkyl-N-ar(lower)alkylamino(-lower)alkoxycarbonyl such as N-lower alkyl-N-phenyl(lower)alkylamino(lower)alkoxycarbonyl [e.g. N-benzyl-N-methylaminomethoxycarbonyl, 1- or 2-(N-benzyl-N-methylamino)ethoxycarbonyl, 1- or 2- or 3-(N-benzyl-N-methylamino)propoxycarbonyl, 2-(N-ethyl-N-phenethylamino)ethoxycarbonyl, etc.], and the like. The preferred examples of said definition may be $C_1$-$C_4$alkoxycarbonyl and N-($C_1$-$C_4$)alkyl-N-phenyl(-$C_1$-$C_4$)alkylamino($C_1$-$C_4$)alkoxycarbonyl, and the most preferred ones are methoxycarbonyl, ethoxycarbonyl, isopropoxycarbonyl and N-benzyl-N-methylaminoethoxycarbonyl.

Suitable "lower alkyl" for R³, $R_a^3$ and R⁴ may include straight or branched one having 1 to 6 carbon atom(s) such as methyl, ethyl, propyl, isopropyl, butyl, isobutyl, tert-butyl, pentyl, tert-pentyl, hexyl and the like, and the preferred example thereof may be $C_1$-$C_4$alkyl and the most preferred one is methyl.

Suitable "acyl" for R³ and $R_c^3$ may include lower alkanoyl such as formyl, acetyl, propionyl, butyryl, isobutyryl, valeryl and the like, and the preferred examples thereof may be $C_1$-$C_4$alkanoyl and the most preferred one is formyl.

"Protected acyl" for R³, $R_a^3$ and $R_b^3$ means the acyl group as stated above, in which the carbonyl group is protected with conventionally employed protective group such as acetal, cyclic acetal and the like. Suitable examples of such protected acyl may include 1,1-di(-lower)alkoxy(lower)alkyl (e.g. dimethoxymethyl, diethoxymethyl, dipropoxymethyl, dibutoxymethyl, 1,1-dimethoxyethyl, 1,1-diethoxyethyl, etc.), 1,1-(lower)alkylenedioxy(lower)alkyl (e.g. 1,3-dioxolan-2-yl, 2-methyl-1,3-dioxolan-2-yl, 2-ethyl-1,3-dioxolan-2-yl, 2-propyl-1,3-dioxolan-2-yl, 1,3-dioxan-2-yl, 2-methyl-1,3-dioxan-2-yl, etc.) and the like, and the preferred ones may be di($C_1$-$C_4$)alkoxymethyl and the most preferred ones are dimethoxymethyl and diethoxymethyl.

Suitable "lower alkylene" for A may include straight or branched one having 1 to 6 carbon atoms such as methylene, ethylene, trimethylene, propylene, tetramethylene, pentamethylene, hexamethylene and the like, in which the preferred one is $C_1$-$C_4$alkylene and the most preferred one is methylene.

The process for the preparation of 2,6-disubstituted-1,4-dihydropyridine derivative and a salt thereof will be explained in detail below.

(1) Process 1:

The compound (I-1) or a salt thereof can be prepared by reacting the compound (II) with the compound (III) or a salt thereof.

Each of the starting compounds (II) and (III) includes cis and trans isomers due to the double bond in its molecule, and both of such isomers can be used as the starting compounds in this process.

The present reaction can be carried out in the absence or presence of a solvent and such solvent may include a conventional one such as benzene, toluene, xylene, chloroform, carbon tetrachloride, methylene chloride, ethylene chloride, methanol, ethanol, butyl alcohol, tert-butyl alcohol, and any other solvent which does not adversely influence the reaction.

The reaction temperature is not critical and the reaction is usually carried out at ambient temperature or under warming or under heating.

As to the reaction mode of this Process, it is to be noted that it can alternatively be carried out, for example, by reacting the compound (II-A), with the compound (II-B) in the presence of the compound (III), and such reaction mode is also included within a scope of this Process.

(2) Process 2:

The compound (I-2) or a salt thereof can be prepared by subjecting the compound (I-1') or a salt thereof to hydrolysis.

The compound (I-1') or a salt thereof can be prepared by the method as illustrated in the above Process 1.

In this process, the protected acyl group for $R_b{}^3$ of the compound (I-1') is transformed into the acyl group.

Hydrolysis may be carried out in a conventional manner which is applicable to cleavage of a so-called acetal function into the corresponding carbonyl function, and preferably, for example, an acidic hydrolysis, i.e. in the presence of an acid such as an inorganic acid (e.g. hydrochloric acid, sulfuric acid, etc.) or an organic acid (e.g. formic acid, acetic acid, trifluoroacetic acid, p-toluenesulfonic acid, etc.), or an acidic ion-exchange resin.

This hydrolysis may be carried out in a suitable conventional solvent such as water, acetone, methyl ethyl ketone, dioxane, ethanol, methanol, N,N-dimethylformamide, dimethylsulfoxide and any other solvent which does not adversely influence the reaction, or buffer solution thereof.

The reaction temperature is not critical, and the reaction is usually carried out under cooling, at room temperature or under somewhat elevated temperature.

(3) Process 3:

The compound (I-3) or a salt thereof can be prepared by reacting the compound (I-2') or a salt thereof with hydroxylamine or a salt thereof and then a dehydrating agent.

According to this process, the formyl group of the starting compound (I-2') is transformed into the hydroxyiminomethyl group (the first step), and in succession said group is transformed into the cyano group (the second step), the reaction schemes of which are shown below.

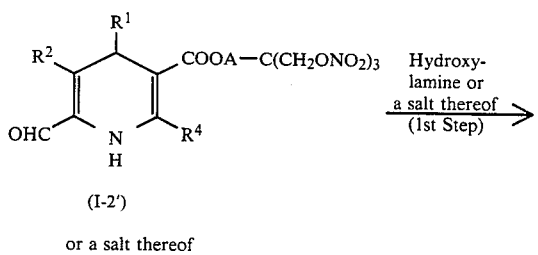

(I-2')

or a salt thereof

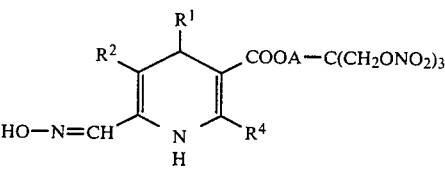

(I-3')

or a salt thereof

Dehydrating Agent (2nd Step)

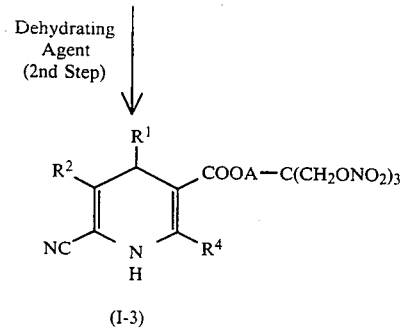

(I-3)

or a salt thereof in which $R^1$, $R^2$, $R^4$ and A are each as defined above.

Preferable salt of hydroxylamine may be a salt with an acid such as an inorganic acid (e.g. hydrochloric acid, sulfuric acid, etc.) or an organic acid (e.g. acetic acid, etc.).

(i) The first step:

The reaction of this step is carried out in a usual manner as so-called oximation reaction, for example, in the presence of a conventional solvent such as water, dioxane, tetrahydrofuran, methanol, ethanol, dimethylformamide, formic acid, acetic acid and any other solvent which does not adversely influence the reaction.

The reaction temperature is not critical and the reaction is usually carried out under cooling, at ambient temperature or under somewhat elevated temperature.

In case that the salt of hydroxylamine is used as the reactant, the reaction is preferably carried out in the presence of a base, suitable examples of which may include an inorganic base such as an alkali metal hydroxide, carbonate or bicarbonate (e.g. sodium hydroxide, potassium hydroxide, sodium carbonate, potassium carbonate, sodium bicarbonate, etc.), an organic base such as an alkali metal alkanoate (e.g. sodium acetate, potassium acetate, etc.), and the like.

The reaction product of the first step is subjected to the following second step with or without isolation and/or purification.

(ii) The second step:

Suitable dehydrating agent used in this step may include conventional organic or inorganic ones such as an organic acid (e.g. formic acid, etc.), an organic acid anhydride (e.g. acetic anhydride, benzoic anhydride, phthalic anhydride, etc.), an organic acid halide (e.g. acetyl chloride, benzoyl chloride, trichloroacetyl chloride, mesyl chloride, tosyl chloride, ethyl chloroformate, phenyl chloroformate, etc.); an inorganic halogen compound (e.g. thionyl chloride, phosphorus pentachloride, phosphorus oxychloride, phosphorus tribromide, stannic chloride, titanium tetrachloride, etc.); a carbodiimide (e.g. N,N'-dicyclohexylcarbodiimide, N-cyclohexyl-N'-morpholinoethylcarbodiimide, etc.), N,N'-carbonyldiimidazole; pentamethyleneketene-N-cyclohexylimine; ethoxyacetylene; 2-ethyl-7-hydroxyisoxazolium salt; other phosphorus compound (e.g. phosphorus pentoxide, polyphosphoric acid ethyl ester, triethylphosphate or phenylphosphate) and the like.

The present reaction can be carried out in the presence of a base such as those given in the above first step and in addition an organic amine base such as trialkylamines (e.g. triethylamine, etc.), pyridine compounds (e.g. pyridine, picoline, lutidine, etc.), N,N-disubstituted benzylamines (e.g. N,N-dimethylbenzylamine, etc.), and the like.

This reaction is usually carried out in a conventional solvent such as diethyl ether, dimethylformamide, pyridine, acetic acid, formic acid, benzene, carbon tetrachloride, chloroform, methylene chloride, tetrahydrofuran, dioxane and any other solvent which does not adversely influence the reaction.

The reaction temperature is not critical and the reaction is usually carried out from at room temperature to under heating.

According to this invention, the object reaction product can be separated and isolated from the reaction mixture and purified by methods commonly used for this purpose, for instance, extraction with suitable solvent, chromatography, precipitation, recrystallization and so on.

The compound (I) thus obtained frequently includes at least one pair of optical isomers due to the presence of an asymmetric carbon atom of the fourth position of the 1,4-dihydropyridine nucleus and can exist as each optical isomer or a mixture thereof. A racemic compound can be resolved into each optical isomer by a conventional method for racemic resolution such as a chemical resolution of the salts of the diastereomer with a conventional optically active acid (e.g. tartaric acid or camphor sulfonic acid, etc.).

It is to be noted that the compound (I) and a pharmaceutically acceptable salt thereof show a nitroglycerin-like action as well as a calcium antagonist-like action and possess a strong and long-lasting vasodilating activities, and therefore are useful for therapeutical treatment in cardiovascular disorder such as coronary insufficiency, angina pectoris and myocardial infarction, and hypertention.

The pharmaceutical composition of this invention comprises, as an active ingredient, the 2,6-disubstituted-1,4-dihydropyridine derivative (I) or a pharmaceutically acceptable salt thereof in an amount of about 0.01 mg to about 1000 mg, preferably about 0.1 mg to about 500 mg per dosage unit for oral and parenteral use.

One skilled in the art will recognize that the amount of the active ingredient in the dosage unit form may be determined by considering the activity of the ingredient as well as the size of the human being. The active ingredient may usually be formulated in a solid form such as tablet, granule, powder, capsule, troche, lozenge or suppository, or a suspension or solution form such as syrup, injection, emulsion, lemonade, etc. and the like. A pharmaceutical carrier or diluent includes solid or liquid, non-toxic pharmaceutically acceptable substances. Examples of solid or liquid carriers or diluents are lactose, magnesium stearate, terra alba, sucrose, corn starch, talc, stearic acid, gelatin, agar, pectin, acacia, peanut oil, olive oil or sesame oil, cacao butter, polyethyleneglycol, hydroxypropyl methylcellulose, or other conventional ones. Similarly, the carrier or diluent may include a time delay material such as glyceryl monostearate, glyceryl distearate, a wax and the like.

Especially, among above dosage unit forms, the formulation comprising the object compound (I) or a pharmaceutically acceptable salt thereof and hydroxypropyl methylcellulose is useful for oral administration.

For the purpose of showing the utility of the compound (I), the pharmacological test result of representative compounds of the present invention is shown in the following.

EFFECT ON ISOLATED CORONARY ARTERY

Test Method

The large coronary arteries, 2.0 mm in outside diameter were removed from pentobarbital-anesthetized dogs. Spiral strips approximately 15 mm in length were cut from the large arteries, and suspended in an organ bath containing calcium-free-Tyrode's solution with EGTA 0.2 mM at 37° C., aerated with a gas mixture of 95% oxygen and 5% carbon dioxide. The tonus of the strips was recorded on a polygraph with a force-displacement transducer. After the initial resting tension was adjusted to 1.0 g for the large artery, potassium fluoride 10 mM was added to the organ bath to increase the tonus of the large arterial strips to 1.4–1.6 g.

The cumulative concentrations of the test compound were then added, and finally paraverine $10^{-4}M$ was given to determine maximum relaxation. $ED_{50}$ values were calculated by interpolation from the mean cumulative dose-activity curves (effect of papaverine $10^{-4}M = 100\%$).

Test Compounds

3-Nitrooxy-2,2-bis(nitrooxymethyl)propyl ester of 4-(2,3-dichlorophenyl)-5-ethoxycarbonyl-2,6-dimethyl-1,4-dihydropyridine-3-carboxylic acid (hereinafter referred to as Compound A), 3-Nitrooxy-2,2-bis(nitrooxymethyl)propyl ester of 6-cyano-5-methoxycarbonyl-2-methyl-4-(3-nitrophenyl)-1,4-dihydropyridine-3-carboxylic acid (hereinafter referred to as Compound B), Dimethyl esters of 2,6-dimethyl-4-(2-nitrophenyl)-3,5-dicarboxylic acid as comparison which is known compound and entitled "Nifedipine" as a generic name.

Test Result

| Test Compounds | $ED_{50}$ values (g/ml) |
| --- | --- |
| A | $9.7 \times 10^{-7}$ |
| B | $1.7 \times 10^{-7}$ |
| Nifedipine | $>1 \times 10^{-6}$ |

Processes for the preparation of the starting compounds (II) and (III) are explained in detail hereinafter.

(A) Process A:

The compound (II) can be prepared by reacting the compound (II-A) with the compound (II-B).

This reaction can be carried out in the absence or presence of the solvent and such solvent may include a conventional one such as benzene, toluene, xylene and any other solvent which does not adversely influence the reaction.

The reaction can preferably be accelerated in the presence of an agent such as an acid (e.g. acetic acid, etc.), a base (e.g. pyridine, picoline, piperazine, piperidine, etc.) or in a conventional buffer solution. These agents act as a reaction accelerator and may also be used as a solvent in case that they are in liquid. The reaction can also be accelerated by warming or heating. The reaction condition may vary according to the kind of the reactants, solvent and/or other agent as mentioned above to be used.

The compound (II-B) in this Process is novel and can be prepared by the following reaction scheme.

$$R_a^4 = \!\!\begin{array}{c} O \\ \square \\ O \end{array} + HO-A-C(CH_2ONO_2)_3 \quad (II-D)$$

(II-C) ↓

$$R^4COCH_2COO-A-C(CH_2ONO_2)_3 \quad (II-B)$$

wherein $R_a^4$ is lower alkylidene such as methylene, ethylidene, propylidene, isopropylidene, and the like, and $R^4$ and A are each as defined above.

And this reaction can usually be carried out in a conventional solvent such as methylene chloride, chloroform and any other solvent which does not adversely influence the reaction under cooling to heating.

(B) Process B:

The compound (III) or a salt thereof can be prepared by reacting the compound (III-A) or a salt thereof with ammonia.

This reaction can usually be carried out in a conventional solvent such as water and any other solvent which does not adversely influence the reaction.

The reaction temperature is not critical and the reaction is usually carried out from under cooling to under warming.

The starting compounds (II) and (III) can be separated or isolated in a conventional manner.

The following examples are given for the purpose of illustrating this invention.

PREPARATION OF THE STARTING COMPOUNDS

Preparation 1

A solution of diketene (2.02 g) in chloroform was added dropwise to a mixture of pentaerythritol trinitrate (5.42 g) and sodium acetate (29 mg) in chloroform (20 ml) over 5 minutes with stirring at 25° C. The resulting mixture was stirred for 3.5 hours at 25° C. and then refluxed for additional 1.5 hours. After cooling to 25° C., the mixture was poured into water. The chloroform layer was separated, dried over anhydrous magnesium sulfate and concentrated under reduced pressure. The residue obtained was recrystallized from a mixture of diethyl ether and ethanol to give 3-nitrooxy-2,2-bis(nitrooxymethyl)propyl ester of acetoacetic acid (4.87 g), mp 59° to 60° C.

IR (Nujol): 1748, 1712, 1658, 1628 cm$^{-1}$

NMR (CDCl$_3$) δ: 2.25 (3H, s), 3.54 (2H, s), 4.31 (2H, s), 4.56 (6H, s).

Elemental analysis for C$_9$H$_{13}$N$_3$O$_{12}$: calcd: C: 30.43, H: 3.69, N: 11.83, found: C: 30.58, H: 3.60, N: 11.58.

Preparation 2

A mixture of methyl 4,4-dimethoxyacetoacetate (8.8 g) and 19.6% methanolic ammonia (21.7 g) was stirred at ambient temperature for 7 hours. After concentration of the reaction mixture, the residual oil (8.6 g) was subjected to distillation under reduced pressure and the product distilled at 95° to 99° C./0.5 mmHg was collected to give methyl 3-amino-4,4-dimethoxyacetoacetate (6.9 g).

IR (Film): 3450, 3330, 2820, 1667, 1620 cm$^{-1}$

NMR (CDCl$_3$) δ: 3.33 (6H, s), 3.65 (3H, s), 4.79 (2H, s), 6.40 (1H, broad).

PREPARATION OF THE OBJECT COMPOUNDS

Example 1

A solution of 2,3-dichlorobenzaldehyde (0.70 g), 3-nitrooxy-2,2-bis(nitrooxymethyl)propyl ester of acetoacetic acid (1.42 g) and methyl 3-amino-crotonate (0.46 g) in tert-butyl alcohol (3 ml) was refluxed for 4.5 hours. The resulting mixture was cooled to 25° C. and then concentrated under reduced pressure. The residue obtained was subjected to column chromatography on silica gel (60 g) and eluted with a mixture of chloroform and methanol (100:1 by volume). The fractions containing the desired compound were collected and evaporated under reduced pressure. The residue obtained was recrystallized from a mixture of diethyl ether and diisopropyl ether to give 3-nitrooxy-2,2-bis(nitrooxymethyl)propyl ester of 4-(2,3-dichlorophenyl)-5-methoxycarbonyl-2,6-dimethyl-1,4-dihydropyridine-3-carboxylic acid (1.11 g), mp 115° to 117.5° C.

IR (Nujol): 3340, 1706, 1654, 1632, 1272, 860 cm$^{-1}$

NMR (CDCl$_3$) δ: 1.95 (3H, s), 2.00 (3H, s), 3.66 (3H, s), 4.24 (2H, s), 4.44 (6H, s), 5.46 (1H, s), 5.92 (1H, s), 7.0–7.5 (3H, m).

Elemental Analysis for C$_{21}$H$_{22}$Cl$_2$N$_4$O$_{13}$: calcd: C: 41.39, H: 3.64, N: 9.19, found: C: 41.71, H: 3.77, N: 8.99.

Example 2

A mixture of 2,3-dichlorobenzaldehyde (0.88 g), 3-nitrooxy-2,2-bis(nitrooxymethyl)propyl ester of acetoacetic acid (1.78 g), acetic acid (50 mg), and piperidine (50 mg) in benzene (10 ml) was refluxed for 1.75 hours, during which time water formed was removed azeotropically. The resulting mixture was cooled, washed successively with water, an aqueous sodium bicarbonate and water, dried over anhydrous magnesium sulfate and concentrated under reduced pressure to give 3-nitrooxy-2,2,-bis(nitrooxymethyl)propyl ester of 2-(2,3-dichlorobenzylidene)acetoacetic acid. Ethyl 3-aminocrotonate was mixed with the product obtained above. The resulting mixture was stirred for 1.5 hours at 80° to 90° C., and then cooled. The mixture in ethyl acetate was washed with an aqueous sodium chloride. The ethyl acetate layer was dried over anhydrous magnesium sulfate and concentrated under reduced pressure. The residue obtained was subjected to column chromatography and eluted with a mixture of ethyl acetate and toluene (1:12 by volume). The fractions containing the desired compound were collected and evaporated under reduced pressure to give yellowish powders. The powders were recrystallized from ethanol to give yellowish crystals of 3-nitrooxy-2,2-bis(nitrooxymethyl)propyl ester of 4-(2,3-dichlorophenyl)-5-ethoxycarbonyl-2,6-dimethyl-1,4-dihydropyridine-3-carboxylic acid (1.39 g), mp 135° to 137° C.

IR (Nujol): 3340, 1707, 1654 cm$^{-1}$

NMR (CDCl$_3$) δ: 1.22 (3H, t, J=7 Hz), 2.29 (3H, s), 2.32 (3H, s), 4.12 (2H, quartet, J=7 Hz), 4.24 (2H, s), 4.44 (6H, s), 5.43 (1H, s), 5.89 (1H, s), 7.1–7.5 (3H, m).

Elemental Analysis for C$_{22}$H$_{24}$Cl$_2$N$_4$O$_{13}$: calcd: C: 42.39, H: 3.88, N: 8.99, found: C: 42.45, H: 3.84, N: 9.13.

Example 3

A solution of 2,3-dichlorobenzaldehyde (0.70 g), 3-nitrooxy-2,2-bis(nitrooxymethyl)propyl ester of acetoacetic acid (1.42 g) and isopropyl 3-aminocrotonate (0.57 g) in tert-butyl alcohol (3 ml) was refluxed for 5.5 hours. The resulting mixture was cooled to 25° C., and then concentrated under reduced pressure. The residue obtained was subjected to column chromatography on silica gel (60 g) and eluted with chloroform. The fractions containing the desired compound were collected and evaporated under reduced pressure to give white powders. The powders were recrystallized from a mixture of diethyl ether and diisopropyl ether to give white crystals of 3-nitrooxy-2,2-bis(nitrooxymethyl)propyl ester of 4-(2,3-dichlorophenyl)-5-isopropoxycarbonyl-2,6-dimethyl-1,4-dihydropyridine-3-carboxylic acid (1.36 g), mp 155° to 156.5° C.

IR (Nujol): 3350, 1700, 1654, 1628, 1272, 857 cm$^{-1}$

NMR (CDCl$_3$) δ: 1.09 (3H, d, J=6 Hz), 1.25 (3H, d, J=6 Hz), 2.30 (6H, s), 4.20 (1H, d, J=12 Hz), 4.33 (1H, d, J=12 Hz), 4.46 (6H, s), 5.03 (1H, heptet, J=6 Hz), 5.43 (1H, s), 5.89 (1H, s), 7.0–7.5 (3H, m).

Elemental Analysis for C$_{22}$H$_{26}$Cl$_2$N$_4$O$_{13}$: calcd: C: 43.34, H:4.11, N: 8.79, found: C: 42.94, H:3.97, N: 8.73.

Example 4

A solution of 2,3-dichlorobenzaldehyde (0.70 g), 3-nitrooxy-2,2-bis(nitrooxymethyl)propyl ester of acetoacetic acid (1.42 g) and 2-(N-benzyl-N-methylamino)ethyl 3-aminocrotonate (0.99 g) in tert-butyl alcohol (3 ml) was heated for 2 hours at 60° C. and then refluxed for additional 5.5 hours. The resulting mixture was cooled to 25° C. and concentrated under reduced pressure. The residue obtained was subjected to column chromatography on silica gel (54 g) and eluted with a mixture of chloroform and methanol (100:1 by volume). The fractions containing the desired compound were collected and evaporated under reduced pressure to give yellow viscous oil. The oil was again subjected to column chromatography on silica gel (27 g) and eluted with a mixture of toluene and ethyl acetate (5:2 by volume). The fractions containing the desired compound were collected and evaporated under reduced pressure. The obtained residue in ethanol was treated with hydrogen chloride in ethanol. The solvent was removed by distillation under reduced pressure to give amorphous yellow powders of 3-nitrooxy-2,2-bis(nitrooxymethyl)propyl ester of 5-[2-(N-benzyl-N-methylamino)ethoxycarbonyl]-4-(2,3-dichlorophenyl)-2,6-dimethyl-1,4-dihydropyridine-3-carboxylic acid hydrochloride (0.40 g).

IR (Nujol): 3150, 1696, 1638, 1272, 847 cm$^{-1}$

NMR (CDCl$_3$) δ: 2.37 (6H, s), 2.4–2.9 (3H, m), 3.30 (2H, broad), 3.9–4.8 (6H, m), 4.49 (6H, s), 5.40 (1H, s), 6.85–7.75 (8H, m), 8.18 (1H, s), 12.2 (1H, broad).

Elemental Analysis for C$_{30}$H$_{33}$Cl$_2$N$_5$O$_{13}$.HCl: calcd: C: 46.26, H:4.40, N:8.99, Cl:13.65, found: C: 45.55, H:4.37, N:8.87, Cl:13.57.

Example 5

A mixture of 2,3-dichlorobenzaldehyde (0.88 g), 3-nitrooxy-2,2-bis(nitrooxymethyl)propyl ester of acetoacetic acid (1.78 g), acetic acid (25 mg), and piperidine (17 mg) in benzene (10 ml) was refluxed for 1.5 hours, during which time water formed was removed azeotropically. The resulting mixture was cooled to 25° C., washed successively with water, an aqueous sodium bicarbonate and water, dried over anhydrous magnesium sulfate, and concentrated under reduced pressure to give 3-nitrooxy-2,2-bis(nitrooxymethyl)propyl ester of 2-(2,3-dichlorobenzylidene)acetoacetic acid. To this product, which was dissolved in tert-butyl alcohol (3 ml), was added 2-(N-benzyl-N-methylamino)ethyl 3-aminocrotonate (1.24 g). The resulting mixture was stirred for 5 hours at 80° C., cooled to 25° C., and then concentrated under reduced pressure. The obtained residue in chloroform (50 ml) was washed twice with 2N hydrochloric acid (10 ml each) and water. The chloroform layer was dried over anhydrous magnesium sulfate and concentrated under reduced pressure to give yellow viscous oil. The oil was subjected to column chromatography on silica gel (90 g) and eluted with a mixture of chloroform and methanol (30:1 by volume). The fractions containing the desired company were concentrated under reduced pressure. The obtained residue in ethanol was treated with hydrogen chloride in ethanol. The solvent was removed by distillation under reduced pressure to give amorphous yellow powders of 3-nitrooxy-2,2-bis(nitrooxymethyl)propyl ester of 5-[2-(N-benzyl-N-methylamino)ethoxycarbonyl]-4-(2,3-dichlorophenyl)-2,6-dimethyl-1,4-dihydropyridine-3-carboxylic acid hydrochloride (1.95 g).

IR (Nujol): 3150, 1696, 1638, 1272, 847 cm$^{-1}$

Elemental Analysis for C$_{30}$H$_{33}$Cl$_2$N$_5$O$_{13}$.HCl: calcd: C:46.26, H:4.40, N:8.99, found: C:46.45, H:4.62, N:8.74.

Example 6

3-Nitrooxy-2,2-bis(nitrooxymethyl)propyl ester of 5-ethoxycarbonyl-2,6-dimethyl-4-(3-nitrophenyl)-1,4-dihydropyridine-3-carboxylic acid (1.42 g) was obtained by reacting 3-nitrobenzaldehyde (0.60 g) with 3-nitrooxy-2,2-bis(nitrooxymethyl)propyl ester of acetoacetic acid (1.42 g) and ethyl 3-aminocrotonate (0.52 g) according to a similar manner to that of Example 1, mp 143° to 145° C.

IR (Nujol): 3340, 1703, 1646, 1273, 860 cm$^{-1}$

NMR (CDCl$_3$) δ: 1.29 (3H, t, J=7 Hz), 2.34 (3H, s), 2.43 (3H, s), 4.17 (1H, d, J=12 Hz), 4.18 (2H, quartet, J=7 Hz), 4.22 (1H, d, J=12 Hz), 4.40 (6H, s), 5.06 (1H, s), 6.23 (1H, s), 7.2–8.2 (4H, m).

Elemental Analysis for C$_{22}$H$_{25}$N$_5$O$_{15}$: calcd.: C:44.08, H:4.20, N:11.68, found: C:43.75, H:4.12, N:11.62.

Example 7

3-Nitrooxy-2,2-bis(nitrooxymethyl)propyl ester of 5-isopropoxycarbonyl-2,6-dimethyl-4-(3-nitrophenyl)-1,4-dihydropyridine-3-carboxylic acid (375 mg) was obtained by reacting 3-nitrobenzaldehyde (151 mg) with 3-nitrooxy-2,2-bis(nitrooxymethyl)propyl ester of acetoacetic acid (355 mg) and isopropyl 3-aminocrotonate (143 mg) according to a similar manner to that of Example 1.

mp 143° to 145° C.

IR (Nujol): 3360, 1700, 1655, 1640, 1276, 854 cm$^{-1}$

NMR (CDCl$_3$) δ: 1.22 (3H, d, J=6 Hz), 1.29 (3H, d, J=6 Hz), 2.37 (3H, s), 2.43 (3H, s), 4.20 (2H, s), 4.39 (6H, s), 5.06 (1H, heptet, J=6 Hz), 5.08 (1H, s), 6.03 (1H, s), 7.3–8.3 (4H, m).

Elemental Analysis for C$_{23}$H$_{27}$N$_5$O$_{15}$: calcd.: C:45.03, H:4.44, N:11.42, found: C:45.16, H:4.42, N:11.32.

Example 8

3-Nitrooxy-2,2-bis(nitrooxymethyl)propyl ester of 5-ethoxycarbonyl-2,6-dimethyl-4-(3-pyridyl)-1,4-dihydropyridine-3-carboxylic acid (1.80 g) was obtained by reacting nicotinaldehyde (0.64 g) with 3-nitrooxy-2,2-bis(nitrooxymethyl)propyl ester of acetoacetic acid (2.13 g) and ethyl 3-aminocrotonate (0.77 g) according to a similar manner to that of Example 1.

mp 136° to 137° C.

IR (Nujol): 3150, 1689, 1645, 1266, 850 cm$^{-1}$

NMR (CDCl$_3$) δ: 1.28 (3H, t, J=7 Hz), 2.30 (3H, s), 2.39 (3H, s), 4.16 (2H, quartet, J=7 Hz), 4.16 (1H, d, J=12 Hz), 4.21 (1H, d, J=12 Hz), 4.95 (1H, s), 6.48 (1H, s), 7.0–8.6 (4H, m).

Elemental Analysis for $C_{21}H_{25}N_5O_{13}$: calcd.: C:45.41, H:4.54, N:12.61, found: C:45.25, H:4.53, N:12.60.

Example 9

A solution of 3-nitrobenzaldehyde (3.02 g), 3-nitrooxy-2,2-bis(nitrooxymethyl)propyl ester of acetoacetic acid (7.10 g) and methyl 3-amino-4,4-dimethoxycrotonate (3.50 g) dissolved in tert-butyl alcohol (12 ml) was refluxed for 15 hours. The resulting mixture was cooled and concentrated under reduced pressure. The residue obtained was subjected to column chromatography on silica gel (200 g) and eluted with a mixture of toluene and ethyl acetate (10:1 by volume). The fractions containing the desired compound were collected and evaporated under reduced pressure to give a viscous oil of 3-nitrooxy-2,2-bis(nitrooxymethyl)propyl ester of 5-methoxycarbonyl-6-dimethoxymethyl-2-methyl-4-(3-nitrophenyl)-1,4-dihydropyridine-3-carboxylic acid (8.60 g).

IR (film): 3370, 2820, 1700, 1640 cm$^{-1}$

NMR (CDCl$_3$) δ: 2.44 (3H, s), 3.37 (3H, s), 3.47 (3H, s), 3.73 (3H, s), 4.21 (2H, s), 4.30 (6H, s), 5.12 (1H, s), 5.96 (1H, s), 6.95–8.20 (5H, m).

Example 10

A solution of 3-nitrooxy-2,2-bis(nitrooxymethyl)propyl ester of 5-methoxycarbonyl-6-dimethoxymethyl-2-methyl-4-(3-nitrophenyl)-1,4-dihydropyridine-3-carboxylic acid (7.50 g) dissolved in a mixture of 6N hydrochloric acid (22.5 ml) and acetone (90 ml) was stirred for 6.5 hours at 20° C. The resulting mixture was evaporated under reduced pressure. The residue obtained was dissolved in ethyl acetate, and washed successively with water, an aqueous sodium bicarbonate and an aqueous sodium chloride. The ethyl acetate solution was dried over anhydrous magnesium sulfate and evaporated under reduced pressure. The residue obtained was subjected to column chromatography on silica gel (200 g) and eluted with a mixture of toluene and ethyl acetate (10:1 by volume). The fractions containing the desired compound were collected and evaporated under reduced pressure and recrystallized from a mixture of ethyl acetate and diisopropyl ether to give yellow crystals of 3-nitrooxy-2,2-bis(nitrooxymethyl)propyl ester of 6-formyl-5-methoxycarbonyl-2-methyl-4-(3-nitrophenyl)-1,4-dihydropyridine-3-carboxylic acid (5.23 g), mp 125° to 125.5° C.

IR (Nujol): 3460, 1708, 1702, 1682, 1650, 1630 cm$^{-1}$

NMR (CDCl$_3$) δ: 2.51 (3H, s), 3.85 (3H, s), 4.16 (1H, d, J=12 Hz), 4.20 (1H, d, J=12 Hz), 4.37 (6H, s), 5.21 (1H, s), 7.15–8.25 (5H, m), 10.40 (1H, s).

Elemental Analysis for $C_{21}H_{21}N_5O_{16}$: calcd: C:42.08, H:3.53, N:11.68, found: C:41.97, H:3.55, N:11.74.

Example 11

To a solution of 3-nitrooxy-2,2-bis(nitrooxymethyl)propyl ester of 6-formyl-5-methoxycarbonyl-2-methyl-4-(3-nitrophenyl)-1,4-dihydropyridine-3-carboxylic acid (3.00 g) in acetic acid (15 ml) were added hydroxylamine sulfate (2:1) (0.49 g) and sodium acetate (0.57 g), followed by stirring at ambient temperature for an hour. To the resulting mixture was added acetic anhydride (15 ml), followed by stirring at ambient temperature for 2 hours and under reflux for additional 2 hours. The reaction mixture was evaporated under reduced pressure and the residue obtained was dissolved in ethyl acetate. This solution was successively washed with water, an aqueous sodium bicarbonate and an aqueous sodium chloride, followed by drying over anhydrous magnesium sulfate. After removal of the solvent, the residual oily product (3.6 g) was subjected to column chromatography using silica gel (90 g). Elution was carried out with a mixture of ethyl acetate and toluene (1:10 to 1:4 by volume) and the fractions containing the desired compound were collected and evaporated to give 3-nitrooxy-2,2-bis(nitrooxymethyl)propyl ester of 6-cyano-5-methoxycarbonyl-2-methyl-4-(3-nitrophenyl)-1,4-dihydropyridine-3-carboxylic acid (1.0 g).

IR (CHCl$_3$): 3405, 2230, 1710, 1652, 1450, 1270, 1084, 832 cm$^{-1}$

NMR (CDCl$_3$) δ: 2.46 (3H, s), 3.83 (3H, s), 4.16 (1H, d, J=8 Hz), 4.26 (1H, d, J=8 Hz), 4.36 (6H, s), 5.19 (1H, s), 7.2–8.25 (5H, m).

Example 12

The object compound in Example 11 (1.0 g) was dissolved in ethanol (150 ml), and to the solution was added hydroxypropyl methylcellulose (5 g) to prepare a suspension. The organic solvent was removed therefrom by distillation to give a solid substance, which was reduced to powder. A proper quantity of this powder was suspended in water or filled up in a capsule.

What we claim is:

1. A compound of the formula:

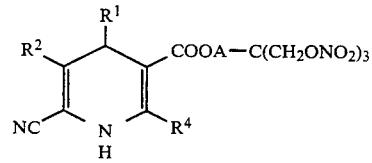

in which
R1 is aryl selected from the group consisting of phenyl, tolyl, xylyl, cumenyl and mesityl which have one or more substituents selected from the group consisting of halogen, nitro, hydroxy, carboxy and lower alkoxy,
R2 is lower alkoxycarbonyl or N-lower alkyl-N-phenyl(lower)alkyl amino(lower)alkoxycarbonyl,
R4 is lower alkyl and
A is lower alkylene,
or pharmaceutically acceptable salt thereof.

2. A compound of claim 1, wherein R1 is phenyl which has one or two substituent(s) selected from halogen and nitro, and
R2 is lower alkoxycarbonyl or N-lower alkyl-N-phenyl(lower)alkylamino(lower)alkoxycarbonyl.

3. A compound of claim 2, wherein R1 is dihalophenyl or nitrophenyl, R2 is lower alkoxycarbonyl or N-lower alkyl-N-phenyl(lower)alkylamino(lower)alkoxycarbonyl.

4. A compound of claim 3, wherein R1 is nitrophenyl, and

R2 is lower alkoxycarbonyl.

5. A compound of claim 4, which is 3-nitrooxy-2,2-bis(nitrooxymethyl)propyl ester of 6-cyano-5-methoxycarbonyl-2-methyl-4-(3-nitrophenyl)-1,4-dihydropyridine-3-carboxylic acid.

6. A vasodilating pharmaceutical composition comprising a vasodilating effective amount of a compound of claim 1 or a pharmaceutically acceptable salt thereof in association with pharmaceutical carrier or diluent.

* * * * *